(12) United States Patent
Ikenaga

(10) Patent No.: US 6,596,833 B2
(45) Date of Patent: Jul. 22, 2003

(54) CARBOSILANE AND POLYCARBOSILANE

(75) Inventor: Kazutoshi Ikenaga, Kumamoto-ken (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/801,722

(22) Filed: Mar. 9, 2001

(65) Prior Publication Data
US 2002/0058747 A1 May 16, 2002

(30) Foreign Application Priority Data
Mar. 14, 2000 (JP) ........................................ 2000-070561

(51) Int. Cl.$^7$ ............................................... C08G 77/60
(52) U.S. Cl. .............................. 528/12; 528/25; 528/35; 556/9
(58) Field of Search ................................. 556/9; 528/35, 528/12, 25

(56) References Cited

PUBLICATIONS

"Organic Chemistry, Fifth Edition", Solomons, 1992, John Wiley and Sons, p. 515.*
"Preparation of New Organosilicon Polymers from Specially Substituted Silyl Triflate Derivatives", Journal of Organometallic Chemistry; Uhlig, W.; 476 (1994) pp. 225–229.*
Bis(trifluoromethylsulfonyloxy)organosilicon Compounds as Synthetic Materials for New Silicon Polymers; Chemische Berichte Uhlig W.; 1194, 127(6), pp. 985–990.*
"Synthesis of Organosilicon Macrocycles. Palladium–catalyzed Ring Enlargement Oligomerization of Cyclic Disilanes via Si–Si sigma–Bond Methathesis." Suginome et al., Organometallics (1996) 15, 2170–78.*
Lee, S.H., et al. "Synthesis and photodegradation of poly [1,4–bis(dimethylsilyl)naphthalene]", Polymer Bulletin, vol. 22 (1989), pp. 355–362.
Iwahara, T., et al. "Synthesis and Properties of Ethynylene–Disilanylene Copolymers", Macromolecules, vol. 23 (1990), pp. 1298–1301.
Ishikawa, M., et al. "Synthesis of poly[(disilanylene)diethynylene] with highly conducting properties", Journal of Organometallic Chemistry, vol. 381 (1990), pp. C57–C59.
Ijadi–Maghsoodi, S., et al. "Synthesis and Study of Silylene– Diacetylene Polymers", Macromolecules, vol. 23 (1990), pp. 4485–4486.
Shiina, K. "The First Successful Ring Opening Polymerization at the Si–Si– Bond: A Novel o–(Disilanylene)phenylene Polymer", Journal of Organometallic Chemistry, vol. 310 (1986), pp. C57–C59.
Ishikawa, M., et al. "Polymeric Organosilicon Systems. 7. Ring–Opening Polymerization of 1,2,5,6–Tetrasilacycloocta–3,7–diynes", Organometallics, vol. 8 (1989), pp. 2741–2742.
Shiina, K., et al. "Thermal Rearrangement of Hexamethyldisilane to Trimethyl(dimethylsilylmethyl)–silane", Journal of Organic Chemistry, vol. 23 (1958), p. 139.
Sakurai, H., et al. "Thermolysis of Hexamethyldisilane", Chemical Communications (1968), p. 930.
Ishikawa, M., et al. "Photolysis of Polymeric Organosilicon Systems. 4. Photochemical Behavior of Poly[p–(disilanylene)phenylene]", Organometallics, vol. 6 (1987), pp. 1673–1679.

* cited by examiner

Primary Examiner—Robert Dawson
Assistant Examiner—Marc S Zimmer
(74) Attorney, Agent, or Firm—Wenderoth, Lind & Ponack, L.L.P.

(57) ABSTRACT

The present invention provides carbosilanes represented by the following general formula (1), polycarbosilanes synthesized therefrom by the polymerization reaction using an organic typical metal compound as an initiator, and the processes for producing the same.

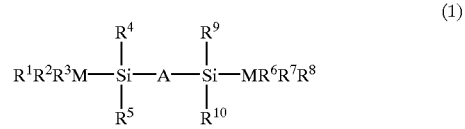

(1)

wherein M represents an Sn, Ge or Pb atom; A represents an aliphatic group having 2–10 carbon atoms, a carbocyclic group or a heterocyclic group containing one or more atoms selected from silicon, oxygen, nitrogen and sulfur atoms, both groups having 6–30 carbon atoms; $R^1$, $R^2$, $R^3$, $R^6$, $R^7$ and $R^8$ each independently represent an alkyl group having 1–20 carbon atoms, an alkenyl or alkynyl group having 2–20 carbon atoms, or an aryl group having 6–20 carbon atoms; $R^4$, $R^5$, $R^9$ and $R^{10}$ each independently represent an alkyl group having 1–20 carbon atoms, an alkenyl or alkynyl group having 2–20 carbon atoms, an alkenylalkyl or alkynylalkyl group having 3–20 carbon atoms, or an aryl group having 6–20 carbon atoms. These carbosilanes and polycarbosilanes per se are useful as industrial materials, but they are also usable as materials for polymers as a macromonomer.

11 Claims, 12 Drawing Sheets

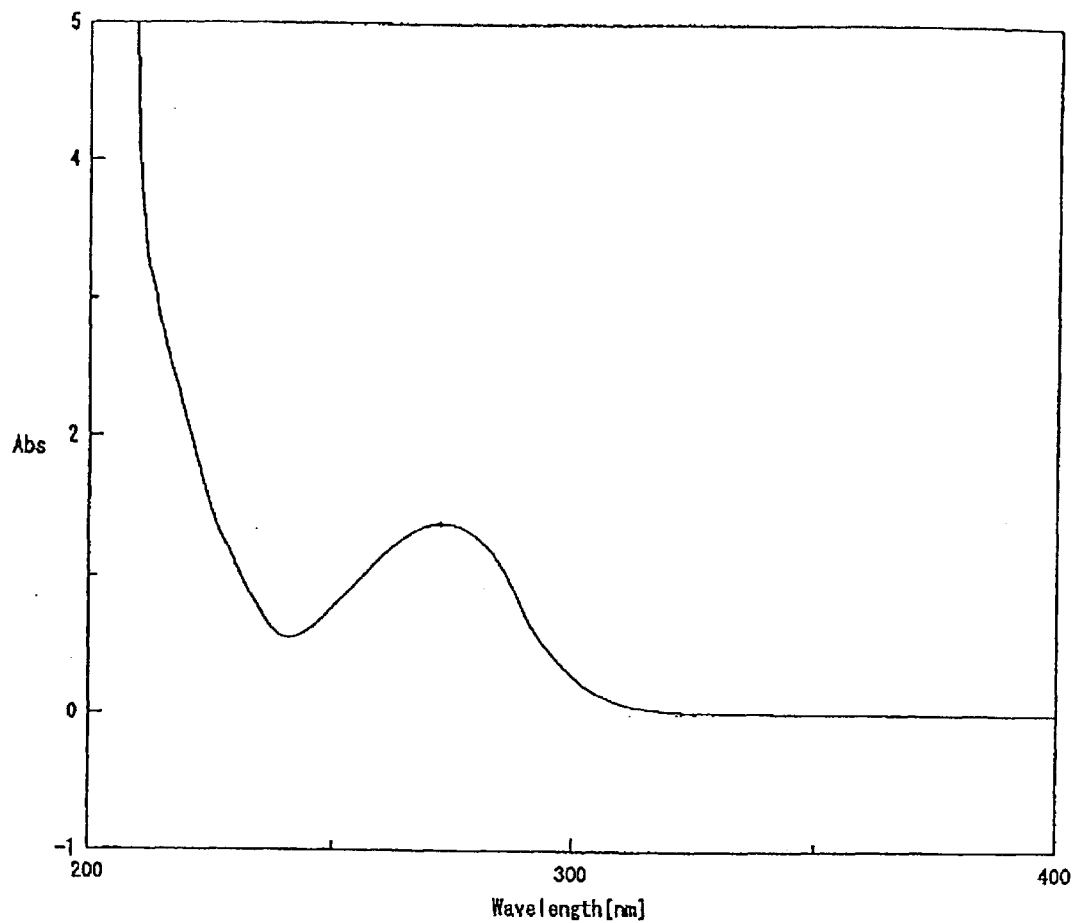
F I G. 10

CARBOSILANE AND POLYCARBOSILANE

FIELD OF THE INVENTION

This is invention relates to novel carbosilanes, polycarbosilanes synthesized therefrom, and the processes for producing the same.

PRIOR ART

Oligocarbosilanes are conventionally prepared by Grignard method or Wurtz method. For example, as reported by K. Nate, M. Ishikawa, H. Ni, H. Watanabe, and Y. Saheki in Organometallics, 6, 1673 (1987), an oligocarbosilane can be prepared by the following reaction.

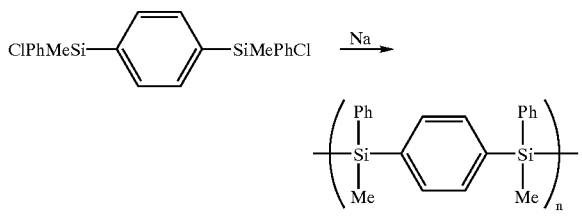

SUMMARY OF THE INVENTION

However, the above method is defective in that a compound having a desired molecular weight can seldom be prepared due to the difficulty in controlling the polymerization degree. The present inventor has studied intensively to improve on the defects of the prior art and finally found that using carbosilanes having specific organometallic groups at their terminals as a starting material can overcome the above problems. This finding has led to the present invention. Further, carbosilanes and polycarbosilanes of the present invention having the organometallic groups of the invention at their terminals are useful organic materials per se and are expected as a new material which is produced by using them as a macromonomer.

The method of the present invention makes it possible to produce polycarbosilanes with polymerization degree controlled by;

(1) using carbosilanes of the present invention having specific organometallic groups containing, e.g., a stannic atom at their terminals, as a starting material, and (2) using organic typical metal compounds such as butyl lithium as an initiator.

By using both the compounds in combination, organometallic groups at the terminals are kept stable after completion of a polymerization reaction. Accordingly, addition of an organic typical metal compound as an initiator can restart the reaction to increase polymerization degree of polycarbosilanes. Polymerization degree of the polycarbosilanes can also be varied by changing the reaction time. The polymerization degree is controllable by these methods.

BRIEF DESCRIPTION OF THE DRAWING

FIG. 10 shows UV analytical chart of polycarbosilane of the invention obtained by the polymerization in Example 9.

DETAILED DESCRIPTION OF THE INVENTION

Figure 1:
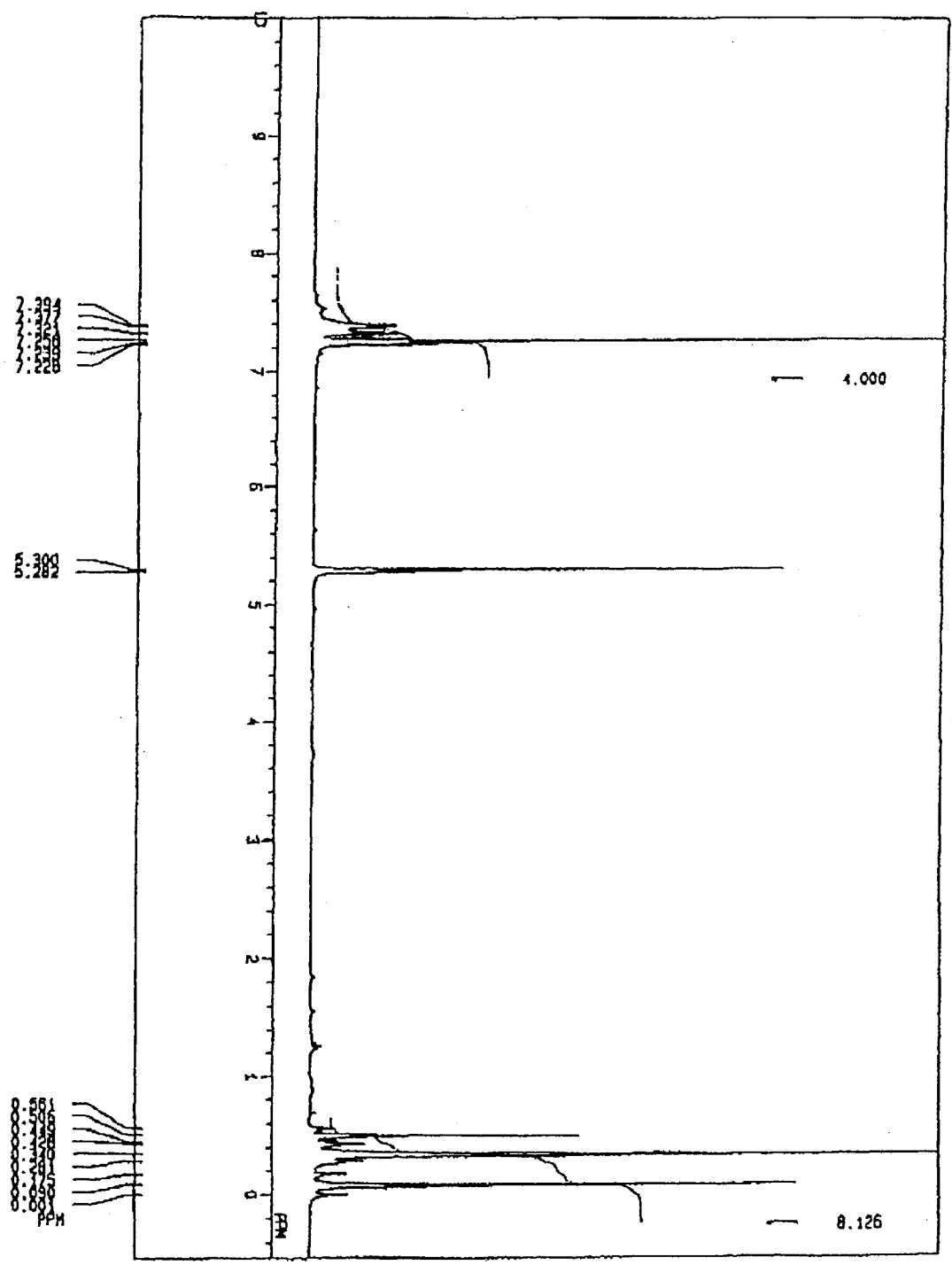
FIG. 1 shows $^1$H-NMR analytical chart of polycarbosilane of the present invention obtained in Example 5.

The present invention is constituted as below.

(1) A carbosilane represented by the following general formula (1):

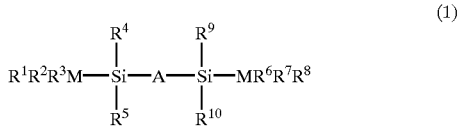

wherein M represents an Sn, Ge or Pb atom; A represents an aliphatic group having 2–10 carbon atoms, a carbocyclic group or a heterocyclic group containing one or more atoms selected from silicon, oxygen, nitrogen and sulfur atoms, both groups having 6–30 carbon atoms; $R^1$, $R^2$, $R^3$, $R^6$, $R^7$ and $R^8$ each independently represent an alkyl group having 1–20 carbon atoms, an alkenyl or alkynyl group having 2–20 carbon atoms, or an aryl group having 6–20 carbon atoms; $R^4$, $R^5$, $R^9$ and $R^{10}$ each independently represent an alkyl group having 1–20 carbon atoms, an alkenyl or alkynyl group having 2–20 carbon atoms, an alkenylalkyl or alkynylalkyl group having 3–20 carbon atoms, or an aryl group having 6–20 carbon atoms.

(2) A carbosilane described in the item (1) in which M represents an Sn atom.

(3) A carbosilane described in the item (1) in which A represents 1,4-phenylene, 2,5-dimethyl-1,4-phenylene, 1,4-xylylene, 1,4-thiophene or 4,4'-biphenylene.

(4) A carbosilane described in the item (1) in which each of $R^1$, $R^2$, $R^3$, $R^4$, $R^5$, $R^6$, $R^7$, $R^8$, $R^9$ and $R^{10}$ is a methyl group.

(5) A polycarbosilane represented by the following general formula (2) whose weight average molecular weight in terms of polystyrene is 800–100,000:

(2)

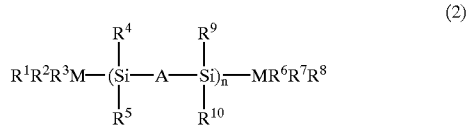

wherein M represents an Sn, Ge or Pb atom; A represents an aliphatic group having 2–10 carbon atoms, a carbocyclic group or a heterocyclic group containing one or more atoms selected from silicon, oxygen, nitrogen and sulfur atoms, both groups having 6–30 carbon atoms; $R^1$, $R^2$, $R^3$, $R^6$, $R^7$ and $R^8$ each independently represent an alkyl group having 1–20 carbon atoms, an alkenyl or alkynyl group having 2–20 carbon atoms, or an aryl group having 6–20 carbon atoms; $R^4$, $R^5$, $R^9$ and $R^{10}$ each independently represent an alkyl group having 1–20 carbon atoms, an alkenyl or alkynyl group having 2–20 carbon atoms, an alkenylalkyl or alkynylalkyl group having 3–20 carbon atoms, or an aryl group having 6–20 carbon atoms; and $1<n\leq 500$.

(6) A polycarbosilane represented by the following general formula (3) whose weight average molecular weight in terms of polystyrene is 800–100,000:

(3)

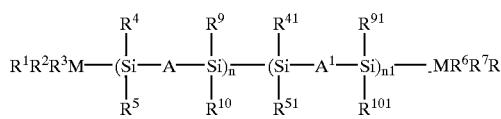

wherein, M represents an Sn, Ge, or Pb atom; A and $A^1$ each independently represent an aliphatic group having 2–10 carbon atoms, a carbocyclic group or a heterocyclic group containing one or more atoms selected from silicon, oxygen, nitrogen and sulfur atoms, both groups having 6–30 carbon atoms; $R^1$, $R^2$, $R^3$, $R^6$, $R^7$ and Re each independently represent an alkyl group having 1–20 carbon atoms, an alkenyl or alkynyl group having 2–20 carbon atoms, or an aryl group having 6–20 carbon atoms; $R^4$, $R^5$, $R^9$, $R^{10}$, $R^{41}$, $R^{51}$, $R^{91}$ and $R^{101}$ each independently represent an alkyl group having 1–20 carbon atoms, an alkenyl or alkynyl group having 2–20 carbon atoms, an alkenylalkyl or alkynylalkyl group having 3–20 carbon atoms, or an aryl group having 6–20 carbon atoms; and $1\leq n\leq 499$, $1\leq n1\leq 499$ and $2\leq n+n1\leq 500$, provided that the two structural units for carbosilane are not identical each other.

(7) A polycarbosilane described in the above item (5) in which M represents an Sn atom.

(8) A polycarbosilane described in the above item (6) in which M represents an Sn atom.

(9) A polycarbosilane described in the above item (5) or (7) in which A represents 1,4-phenylene, 2,5-dimethyl-1,4-phenylene, 1,4-xylylene, 1,4-thiophene or 4,4'-biphenylene.

(10) A polycarbosilane described in the above item (6) or (8) in which A represents 1,4-phenylene, 2,5-dimethyl-1,4-phenylene, 1,4-xylylene, 1,4-thiophene or 4,4'-biphenylene.

(11) A process for producing a polycarbosilane represented by the general formula (2)

(2)

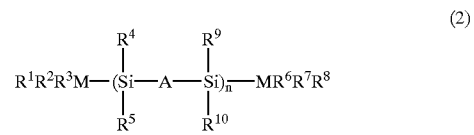

wherein M represents an Sn, Ge or Pb atom; A represents an aliphatic group having 2–10 carbon atoms, a carbocyclic group or a heterocyclic group containing one or more atoms selected from silicon, oxygen, nitrogen and sulfur atoms, both groups having 6–30 carbon atoms; $R^1$, $R^2$, $R^3$, R , $R^7$ and $R^8$ each independently represent an alkyl group having 1–20 carbon atoms, an alkenyl or alkynyl group having 2–20 carbon atoms, or an aryl group having 6–20 carbon atoms; $R^4$, $R^5$, $R^9$ and $R^{10}$ each independently represent an alkyl group having 1–20 carbon atoms, an alkenyl or alkynyl group having 2–20 carbon atoms, an alkenylalkyl or alkynylalkyl group having 3–20 carbon atoms, or an aryl group having 6–20 carbon atoms; and $1<n\leq 500$, or the general formula (3)

(3)

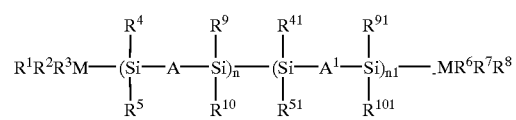

wherein M, A, $R^1$, $R^2$, $R^3$, $R^4$, $R^5$, $R^6$, $R^7$, $R^8$, $R^9$ and $R^{10}$ are as defined above; $A^1$ has the same meaning as A; $R^{41}$, $R^{51}$, $R^{91}$ and $R^{101}$ have the same meaning as $R^4$, $R^5$, $R^9$ and $R^{10}$, respectively; and $1\leq n\leq 499$, $1\leq n1\leq 499$ and $2\leq n+n1\leq 500$, provided that the two structural units for carbosilane are not identical each other, which comprises reacting the same or different kinds of carbosilanes represented by the general formula (1)

(1)

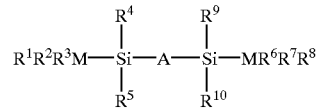

wherein M, A, $R^1$, $R^2$, $R^3$, $R^4$, $R^5$, $R^6$, $R^7$, $R^8$, $R^9$ and $R^{10}$ are as defined above, using an organic typical metal compound as an initiator.

Carbosilanes represented by the general formula (1) can be synthesized, for instance, according to the following scheme. Polycarbosilanes of the present invention can be prepared by reacting the carbosilanes thus obtained, using an organic typical metal compound as an initiator.

The carbosilane of the present invention includes those from oligomer to polymer, having a weight average molecular weight in terms of polystyrene of 800–100,000.

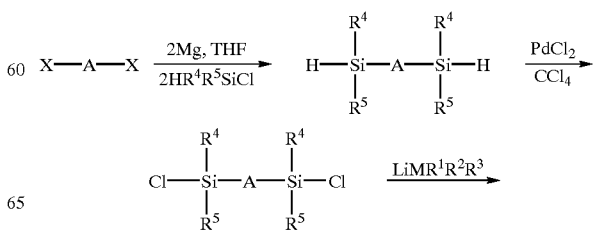

-continued

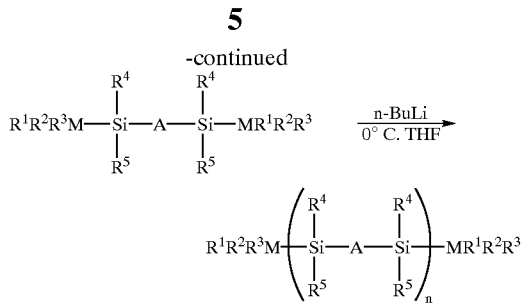

(In the above formulas, M, A, $R^1$, $R^2$, $R^3$, $R^4$, $R^5$ and n are as described above.)

Chemical formulas of the carbosilane and polycarbosilane are simplified in the above scheme, and therefore, they are not necessarily identical with those of the formulas (1) and (2). However, use of two kinds of chlorosilanes and two kinds of organic typical metal compounds in the reaction may result in the compounds of formulas (1) and (2) wherein $R^1$ to $R^{10}$ are not identical each other.

In the compounds represented by the general formula (1), (2) or (3), $R^1$, $R^2$, $R^3$, $R^4$, $R^5$, $R^6$, $R^7$, $R^8$, $R^9$, $R^{10}$, $R^{41}$, $R^{51}$, $R^{91}$ and $R^{101}$ are substituents of silicon or a tetravalent metal as described above. Among them, an alkyl group preferably has 1–6 carbon atoms, an alkenyl or alkynyl group preferably has 2–6 carbon atoms, and an aryl group preferably has 6–12 carbon atoms. For $R^1$, $R^2$, $R^3$, $R^6$, $R^7$ and $R^8$ which are substituents of a tetravalent metal, preferably at least one of them is a methyl or ethyl group and more preferably all of them are a methyl or ethyl group.

In the general formulas (1), (2) and (3), M represents an Sn, Ge or Pb atom, and most preferably Sn.

Further, for divalent groups A and $A^1$ as described above, "a carbocyclic group" means a group which contains as an essential component at least one selected from a monocyclic hydrocarbon group, a condensed polycyclic hydrocarbon group and a cross-linked cyclic hydrocarbon group of an alicyclic or aromatic hydrocarbon. If necessary, these groups may be substituted or cross-linked with an optional substituent or a cross-linking group, for example, a hydrocarbon group, a hydrocarbon group having at least one selected from silicon, oxygen, sulfur and nitrogen atoms, or a sulfone group. Preferred examples include 1,4-phenylene, 2,5-dimethyl-1,4-phenylene, 1,4-xylylene, 1,4-thiophene and 4,4'-biphenylene. Among them, 1,4-thiophene has an excellent solubility to solvent.

Concrete examples of the carbosilane represented by the general formula (1) are illustrated below.

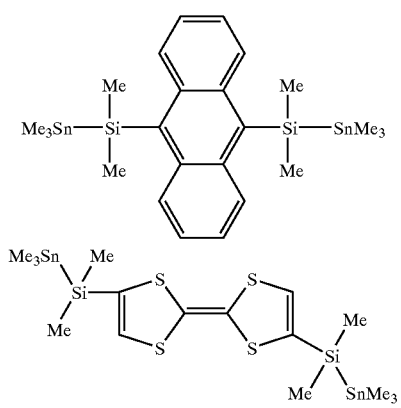

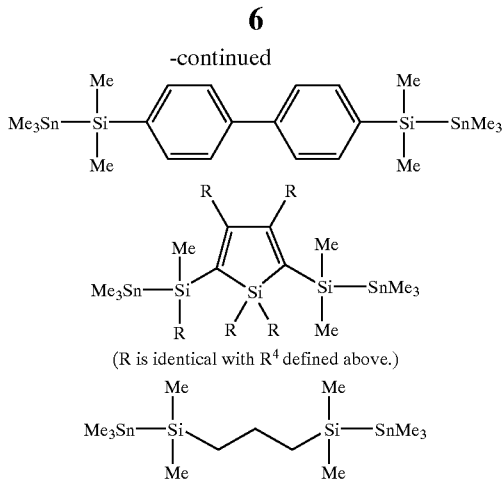

(R is identical with $R^4$ defined above.)

The polycarbosilane of the present invention can be prepared by polymerizing carbosilanes having organometallic groups at their terminals, which are synthesized by the method described above, using an organic typical metal compound as an initiator. As already stated, in the polycarbosilane of the present invention, the organometallic groups at their terminals is kept stable after the polymerization reaction. Thus, the reaction proceeds further when an initiator is added. Alternatively, polymerization degree of the polycarbosilane can also be controlled by changing polymerization time.

A polymer can be synthesized from a single material, whereas a random copolymer can be prepared by polymerizing two or more kinds of carbosilanes with mixing them at the initial stage of the polymerization. Using the latter method, a polymer having an excellent solubility to solvent can be synthesized. Alternatively, in order to obtain a polymer having respective physical properties of two different kinds of polymers, both the polymers that have been synthesized separately are mixed and allowed to react in the presence of an initiator to prepare a block copolymer.

The organic group of the organic typical metal compound used as a polymerization initiator is an alkyl group having 1–20 carbon atoms, preferably 1–6 carbon atoms, an alkenyl or alkynyl group having 2–20 carbon atoms, preferably 2–6 carbon atoms, or an aryl group having 6–20 carbon atoms, preferably 6–12 carbon atoms. The typical metal is lithium, sodium, magnesium, calcium or zinc, and preferably lithium. Among lithium compounds, butyl lithium and methyl lithium are preferable. In case of a polyvalent metal compound, at least one of the substituents should be selected from the above organic groups.

In the process according to the present invention, the reaction can be carried out in a solvent. The solvent is not restricted unless it reacts with the starting compounds and as far as it can dissolve the starting compounds. For example, generally used solvents, e.g., ethers such as tetrahydrofuran, dioxane, ethyleneglycol diethylether, diethyleneglycol dimethylether; aliphatic and alicyclic hydrocarbons such as hexane, heptane and cyclohexane; and aromatic hydrocarbons such as toluene and xylene, may be used alone or in combination. The reaction temperature is −40 to 30° C., preferably −20 to 10° C.

Carbosilane or polycarbosilane of the present invention thus prepared can be used for a liquid crystalline compounds, a conductive material, a sensor material such as a light switching element and a memory element, a functional material such as an organic photosensitive material, a light memory material, and a ceramic precursor.

The present invention shall be explained below in detail with reference to examples, but the present invention shall not be restricted to these examples.

EXAMPLE 1

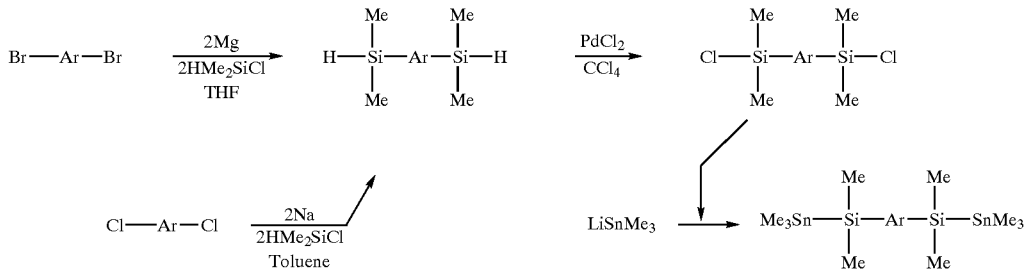

(1) Preparation of 1,4-bis(dimethylhydrosilyl)benzene

Into a 500 ml three-necked flask equipped with two dropping funnels and a refluxing condenser was introduced 5.35 g (220 mmol) of shaved magnesium and then air was purged with nitrogen. 150 ml of anhydrous THF was introduced into the flask under nitrogen atmosphere. The mixture was stirred vigorously to make a uniform solution. 23.6 g (100 mmol) of 1,4-dibromobenzene and anhydrous THF (25.0 ml) were introduced in one dropping funnel, and 25.5 ml (230 mmol) of dimethylchlorosilane was introduced into the other funnel. About 3.0 ml each of the solutions was dropped into the flask and the flask was heated using a dryer. About 10 minutes later, the solution began to reflux, and then the remaining parts of the solutions in the funnels were dropped into the flask while keeping it warm. After dropping was completed, the solution was heated to reflux for about 30 minutes using a hotting magnetic stirrer. After cooling the flask in an ice bath, 60.0 ml of ether was added to the flask. The solution wan Sneutralized by 100 ml of saturated aqueous $NH_4Cl$, followed by hydrolysis. Then, magnesium salt was filtered off using Celite-ether, the resultant solution was extracted with 100 ml of ether, and dried over anhydrous $MgSO_4$. After drying, the desiccating agent was filtered off, the solvent was removed by distillation under atmospheric pressure and reduced pressure to obtain a concentrated solution. Then, 1,4-bis(dimethylhydrosilyl) benzene of the objective substance was obtained by distillation under reduced pressure using a distillation column packed with beads for fractionating distillation. A stretching vibration due to Si-H bondage at 2100 $cm^{-1}$ was confirmed by IR measurement. Distillation condition was 102–104° C./16 mmHg and yield was 11.3 g (41%).

(2) Chlorination Reaction of a Hydrosilyl Group 1,4-bis(dimethylhydrosilyl)-benzene was introduced into a nitrogen-purged round bottom flask equipped with a reflux condenser. Then, 45.0 ml of anhydrous $CCl_4$ was fed into the flask under nitrogen atmosphere to make a uniform solution. 0.021 g (0.12 mmol) of $PdCl_2$ was added to the solution, which was then heated to reflux using an oil bath for about 3 hours. The reaction solution was then cooled down to room temperature and a part of the solution was taken out by a micro syringe for gas chromatograph analysis to confirm the completion of the reaction. The solvent was removed under reduced pressure, and thereafter the chloride was isolated using Kugelrohr distillation equipment. Distillation was performed using a nitrogen-purged receiver to avoid contamination by air as much as possible to obtain the aimed substance 1,4-bis(dimethylchlorosilyl)benzene. After the distillation was over, the compound thus obtained was preserved under equipment with a nitrogen balloon until the next reaction begins. Distillation condition was 80–110° C./0.9 mmHg and yield was 90%. For the next reaction, the receiver was connected with the reactor, into which the compound was flowed with anhydrous THF.

(3) Preparation of Trimethylstanyllithium

Into a nitrogen-purged 200 ml three-necked flask equipped with a 100 ml dropping funnel and a thermometer were introduced under argon gas atmosphere 80 ml of anhydrous THF and 400 mmol of metal lithium cut into small pieces from lump. In the dropping funnel was fed a 100 ml of a THF solution of $Me_3SnCl$ (1 mol/L), and the flask was cooled to a temperature of −3 to 0° C. in an ice-salt bath. 20–30 minutes after dropwise addition of about 5.0 ml of the solution, temperature of the solution in the flask was raised to 0 to 1° C., and the color turned into yellowish green. Then, the rest of the solution was added dropwise over about 1.5 hours while maintaining the temperature at −3 to 0° C.

(4) Preparation of a bis(stanylsilyl) Compound (a) Preparation of 1,4-bis(dimethyltrimethylstanylsilyl) benzene Into a nitrogen-purged 300 ml three-necked flask with a 100 ml dropping funnel were introduced under argon atmosphere 60 ml of anhydrous THF and 50 mmol of 1,4-bis (dimethylchlorosilyl)benzene to form a uniform solution. A THF solution of stanylsilyllithium was injected into the dropping funnel through a syringe, and the flask was cooled to about 0° C. in an ice-salt bath. Then the solution was dropped into the flask while maintaining the temperature not to exceed 0° C. After dropping was finished, the reaction mixture was left to stir for 20–30 minutes, then a part of the reaction mixture was taken out using a micro syringe for gas chromatograph analysis to confirm the completion of the reaction. The solvent was distilled off under reduced pressure, lithium chloride was filtered off using 100 ml of Celite-hexane, and then the solution was dried over anhydrous $MgSO_4$. After drying was over, the solution was concentrated to remove the solvent under reduced pressure, and the residue was distilled under reduced pressure through a distillation column packed with beads for fractionation to obtain 15.6 g of 1,4-bis(dimethyltrimethylstanylsilyl) benzene as a white solid (b.p., 98–130° C./1.3 mmHg; yield, 60%). The molecular structure of the product was determined from the analytical results of $^1H$-NMR, $^{13}C$-NMR, IR and GC. The product was recrystallized from hexane to give white crystals (m.p., 97–98° C.).

EXAMPLES 2–4

Using 2,5-dimethy-1,4-dibromobenzene, 1,4-bis (bromomethyl)benzene or 1,4-dibromothiophene, instead of 1,4-dibromobenzene used in Example 1(1), reactions were carried out in the same manner as in Example 1(1) to afford 2,5-dimethyl-1,4-bis(dimethylhydrosilyl)benzene, 1,4-bis(dimethylhydrosilylmethyl)benzene or 1,4-bis(dimethylhydrosilyl)thiophene, respectively. Distillation conditions and yield are shown in Table 1.

TABLE 1

Preparation of bis(hydrosilyl) compounds

| Example | HSi—Ar—SiH | Distillation condition | Yield |
|---|---|---|---|
| 2 | 2,5-dimethyl-1,4-bis-(dimethylhydrosilyl)-benzene | 75–76° C./ 1.7 mmHg | 54% |
| 3 | 1,4-bis(dimethylhydrosilylmethyl)benzene | 61–62° C./ 1.1 mmHg | 65% |
| 4 | 1,4-bis(dimethylhydrosilyl)thiophene | 95–96° C./ 1.8 mmHg | 80% |

Using 2,5-dimethy-1,4-bis(dimethylhydrosilyl)benzene, 1,4-bis(dimethylhydrosilylmethyl)benzene or 1,4-bis(dimethylhydrosilyl)thiophene, instead of 1,4-bis(dimethylhydrosilyl)benzene used in Example 1(2), reactions were carried out in the same manner as in Example 1(2) to afford 2,5-dimethyl-1,4-bis(dimethylchlorosilyl)benzene, 1,4-bis(dimethylchlorosilylmethyl)benzene or 1,4-bis(dimethylchlorosilyl)thiophene, respectively.

Distillation conditions and yield are shown in Table 2.

TABLE 2

| Example | ClSi—Ar—SiCl | Distillation condition | Yield |
|---|---|---|---|
| 2 | 2,5-dimethyl-1,4-bis-(dimethylchlorosilyl)-benzene | 72–100° C./ 0.8 mmHg | 83% |
| 3 | 1,4-bis(dimethylchlorosilylmethyl)benzene | 90–100° C./ 1.1 mmHg | 96% |
| 4 | 1,4-bis(dimethylchlorosilyl)thiophene | 65–82° C./ 1.8 mmHg | 67% |

Further, using 2,5-dimethyl-1,4-bis(dimethylchlorosilyl)benzene, 1,4-bis(dimethylchlorosilylmethyl)benzene or 1,4-bis(dimethylchlorosilyl)thiophene, instead of 1,4-bis(dimethylchlorosilyl)benzene used in Example 1(4)(a), reactions were carried out in the same manner as in Example 1(4)(a) to afford 2,5-dimethyl-1,4-bis(dimethyltrimethylstanylsilyl)benzene, 1,4-bis(dimethyltrimethylstanylsilylmethyl)benzene or 1,4-bis(dimethyltrimethylstanylsilyl)thiophene, respectively. Distillation conditions and yield are shown in Table 3.

TABLE 3

| Example | Bis(Stanylsilyl) Compound | Distillation Condition | Yield |
|---|---|---|---|
| 2 | 2,5-dimethyl-1,4-bis-(dimethyltrimethylstanyl-silyl)benzene | 120–180° C./ 1.4 mmHg | 25%*[1] |
| 3 | 1,4-bis(dimethyltrimethylstanylsilylmethyl)-benzene | 116–180° C./ 1.4 mmHg | 21%*[2] |
| 4 | 1,4-bis(dimethyltrimethylstanylsilyl)-thiophene | 100–120° C./ 1.5 mmHg | 43% |

*[1] m.P. 107–108° C.
*[2] m.p. 50–52° C.

EXAMPLE 5

Polymerization Reaction of bis(stanylsilyl) Compounds

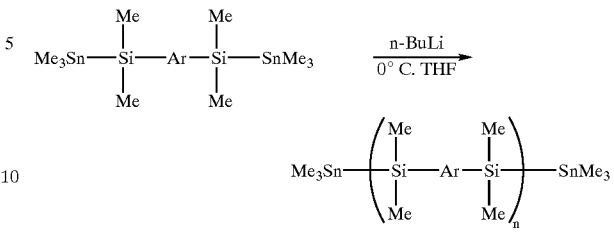

Figure 2:
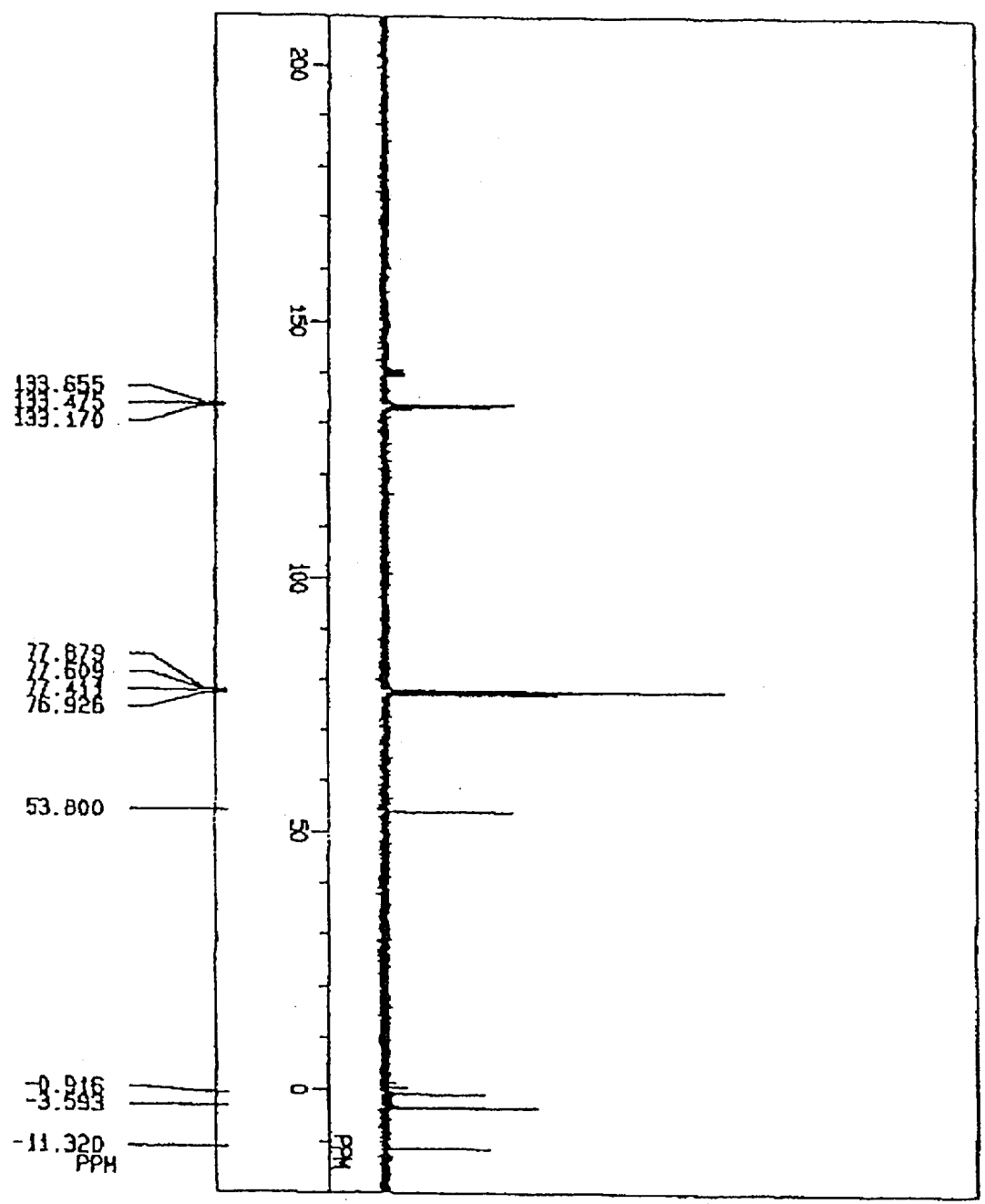
FIG. 2 shows $^{13}$C-NMR analytical chart of polycarbosilane of the invention obtained in Example 5.

Into a nitrogen-purged 30 ml three-necked flask equipped with a septum cap and a digital thermometer was introduced 1.2 g (2.0 mmol) of 1,4-bis(dimethyltrimethylstanylsilyl)benzene, then 10.0 ml of anhydrous THF was added under argongas atmosphere to form a uniform solution. The flask was cooled to −10° C., to which 0.8 ml (1.0 mmol) of n-BuLi was added using a micro syringe, and the solution became whitely clouded. The solution was left to stand for about 30 minutes, and then a part of the solution was taken out using a micro syringe for GC analysis to confirm complete consumption of the material. After the reaction was over, the solvent was removed under reduced pressure, 20 ml of hexane was added to carry out a suck filtration to recover an insoluble solid. The solid thus obtained was washed with water and dried in a desicator. The mother liquid was concentrated under reduced pressure, then filtered using 40 ml of Celite-hexane to obtain hexane solubles and THF solubles, separately. Both the solubles were concentrated under reduced pressure to obtain 0.46 g of hexane solubles, 0.17 g of THF solubles and 0.18 g of insoluble solid. Analytical results of these compounds are shown in Table 4. $^1$H-NMR analytical chart is shown in FIG. 1 and $^{13}$C-NMR analytical chart is shown in FIG. 2.

EXAMPLES 6–7

Using 2,5-dimethyl-1,4-bis(dimethyltrimethylstanylsilyl)benzene (Example 6) or 1,4-bis(dimethyltrimethylstanylsilylmethyl)benzene (Example 7), instead of 1,4-bis(dimethyltrimethylstanylsilyl)benzene in Example 5, reactions were carried out in the same manner as in Example 5 to prepare respective polymers. The results are shown in Table 4.

Figure 3:
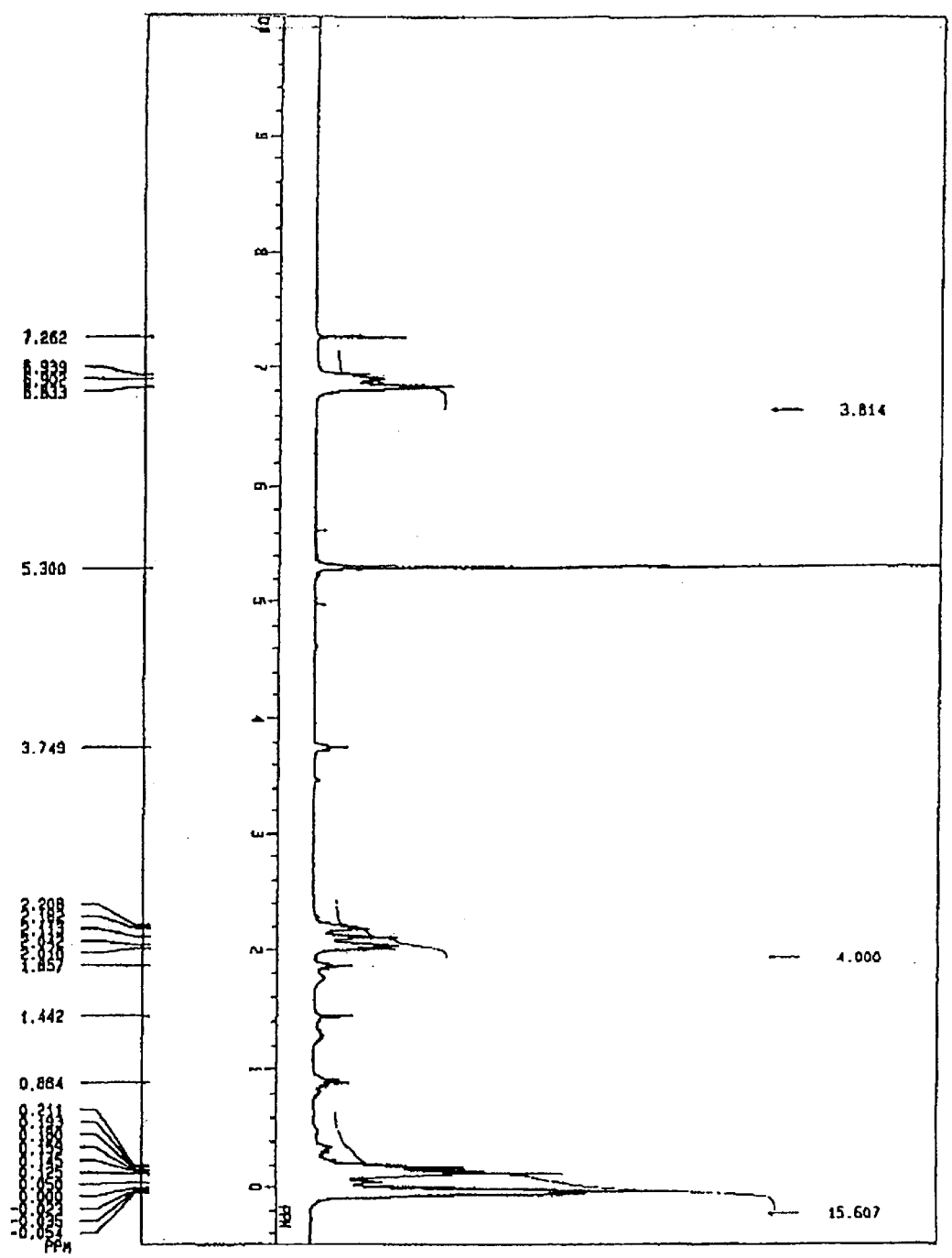
FIG. 3 shows $^1$H-NMR analytical chart of polycarbosilane of the invention obtained in Example 7.
Figure 4:
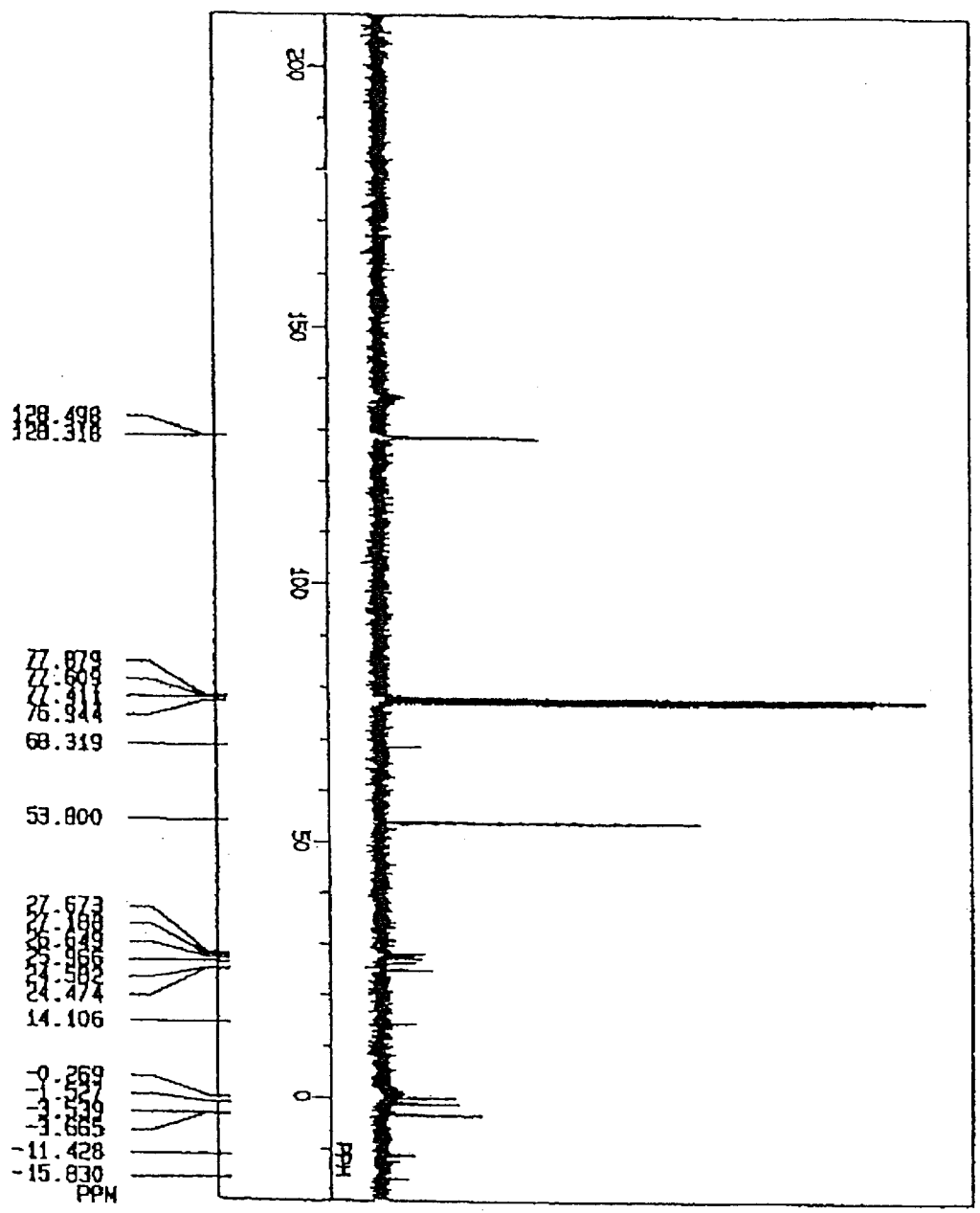
FIG. 4 shows $^{13}$C-NMR analytical chart of polycarbosilane of the invention obtained in Example 8.

$^1$H-NMR analytical chart of the polymer obtained in Example 7 is shown in FIG. 3 and $^{13}$C-NMR analytical chart is shown in FIG. 4.

EXAMPLE 8

Using 1,4-bis(dimethyltrimethylstanylsilyl)thiophene instead of 1,4-bis(dimethyltrimethylstanylsilyl)benzene in Example 5, a reaction was carried out in the same manner as in Example 5 to prepare a polymer. The results are shown in Table 4.

Table 4 shows that the molecular weight of the resulting polymer increased due to additional polymerization reactions by further adding an initiator. The average molecular weight in terms of polystyrene which was measured by GPC using THF as an eluent are as follows.

After the first step reaction:
  Mn=1237, Mw=1631, Mz=2084
  Mw/Mn=1.3185, Mz/Mn=1.6853
After the second step reaction:
  Mn=2155, Mw=2913, Mz=4193
  Mw/Mn=1.3516, Mz/Mn=1.9454

Figure 5:
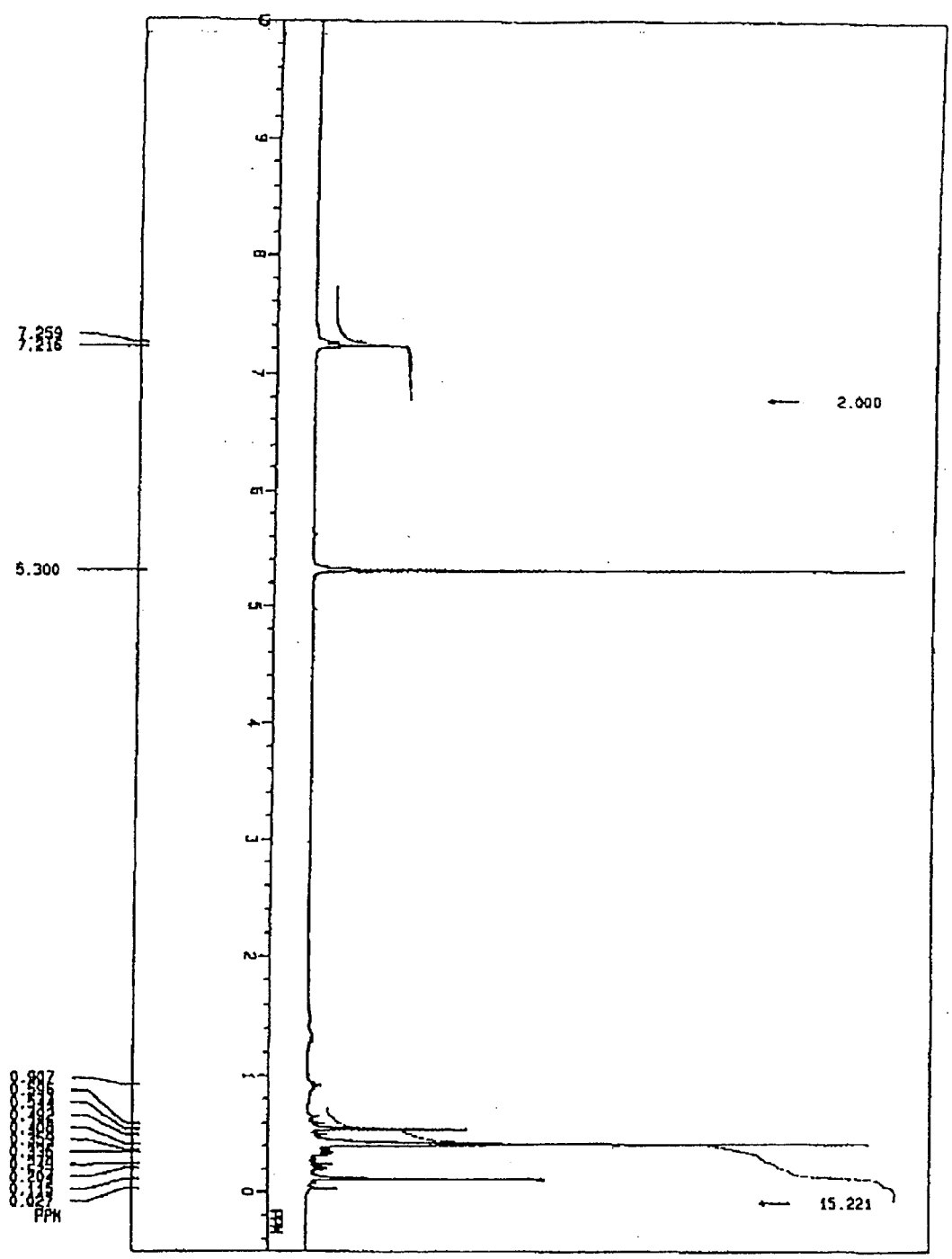
FIG. 5 shows $^1$H-NMR analytical chart of polycarbosilane of the invention obtained by the initial polymerization in Example 8.
Figure 6:
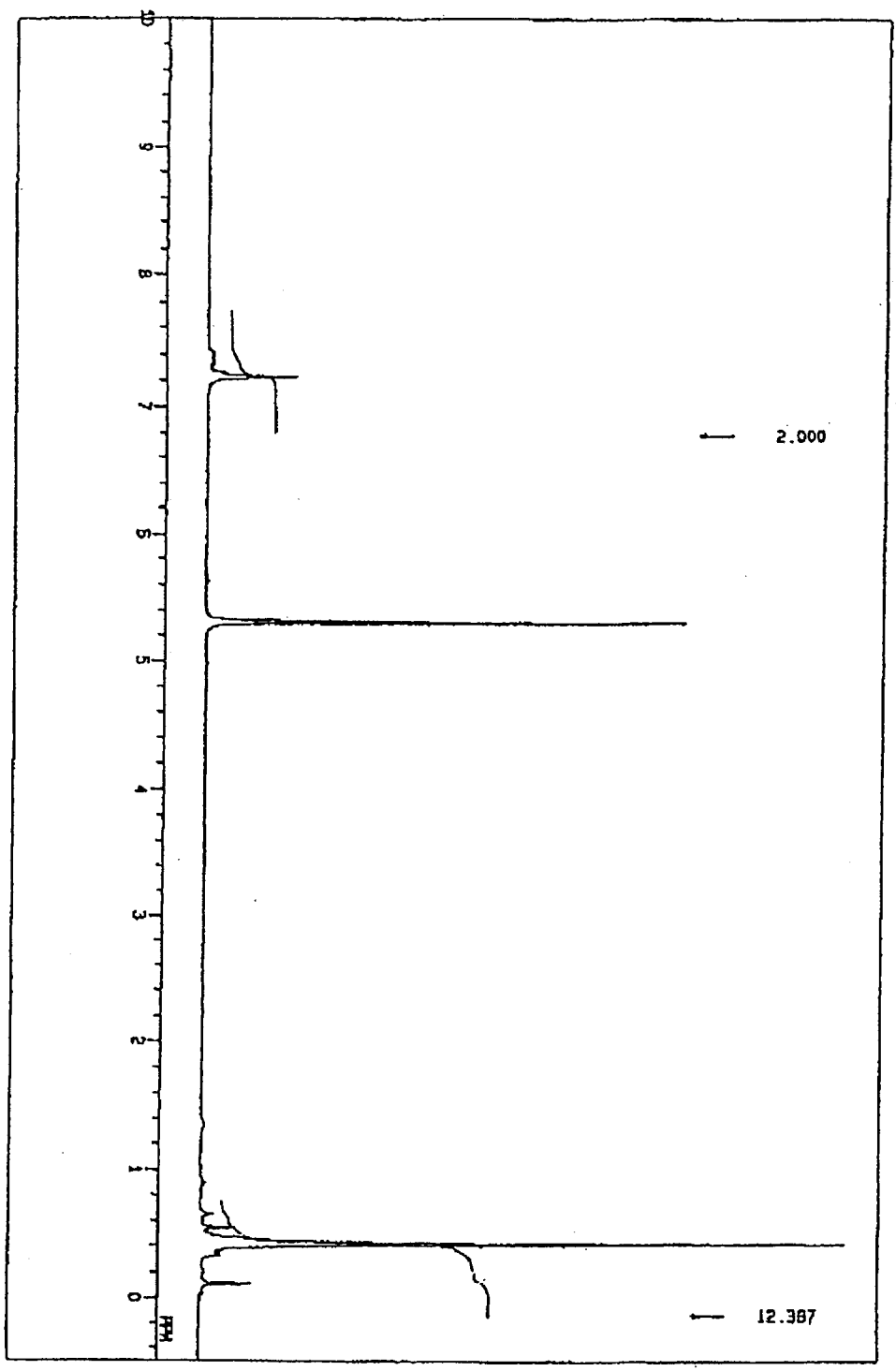
FIG. 6 shows $^1$H-NMR analytical chart of polycarbosilane of the invention obtained by the additional polymerization in Example 8.
Figure 7:
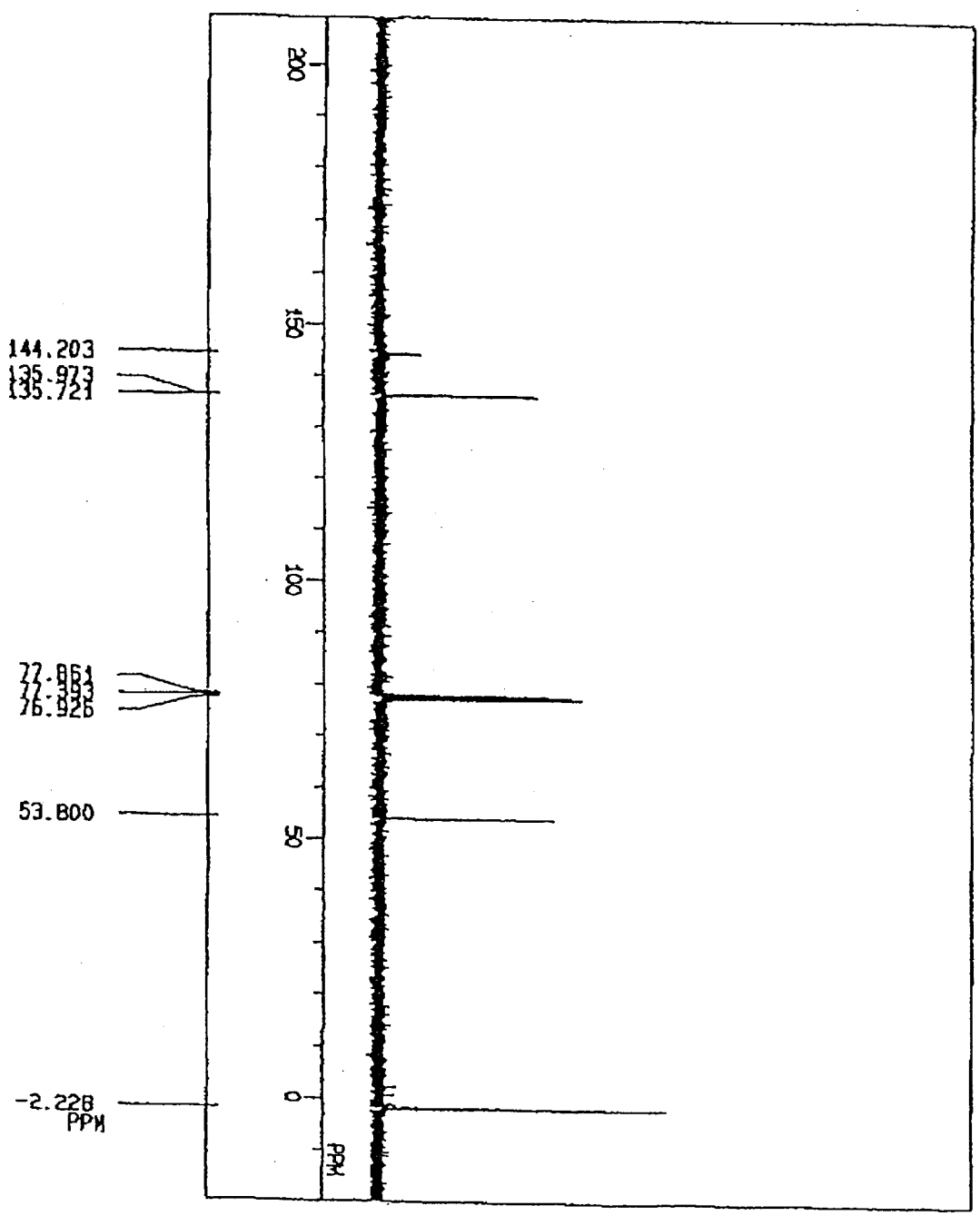
FIG. 7 shows $^{13}$C-NMR analytical chart of polycarbosilane of the invention obtained by the additional polymerization in Example 8.

¹H-NMR analytical charts of the polymer obtained in the first step and second step reactions are shown in FIG. 5 and FIG. 6, respectively, and ¹³C-NMR analytical chart is shown in FIG. 7.

EXAMPLE 9

Using 4,4'-bis(dimethyltrimethylstanylsilyl)biphenyl instead of 1,4-bis(dimethyltrimethylstanylsilyl)benzene in Example 5, a reaction was carried out in the same manner as in Example 5 to prepare a polymer. The results are shown in Table 4.

Figure 8:
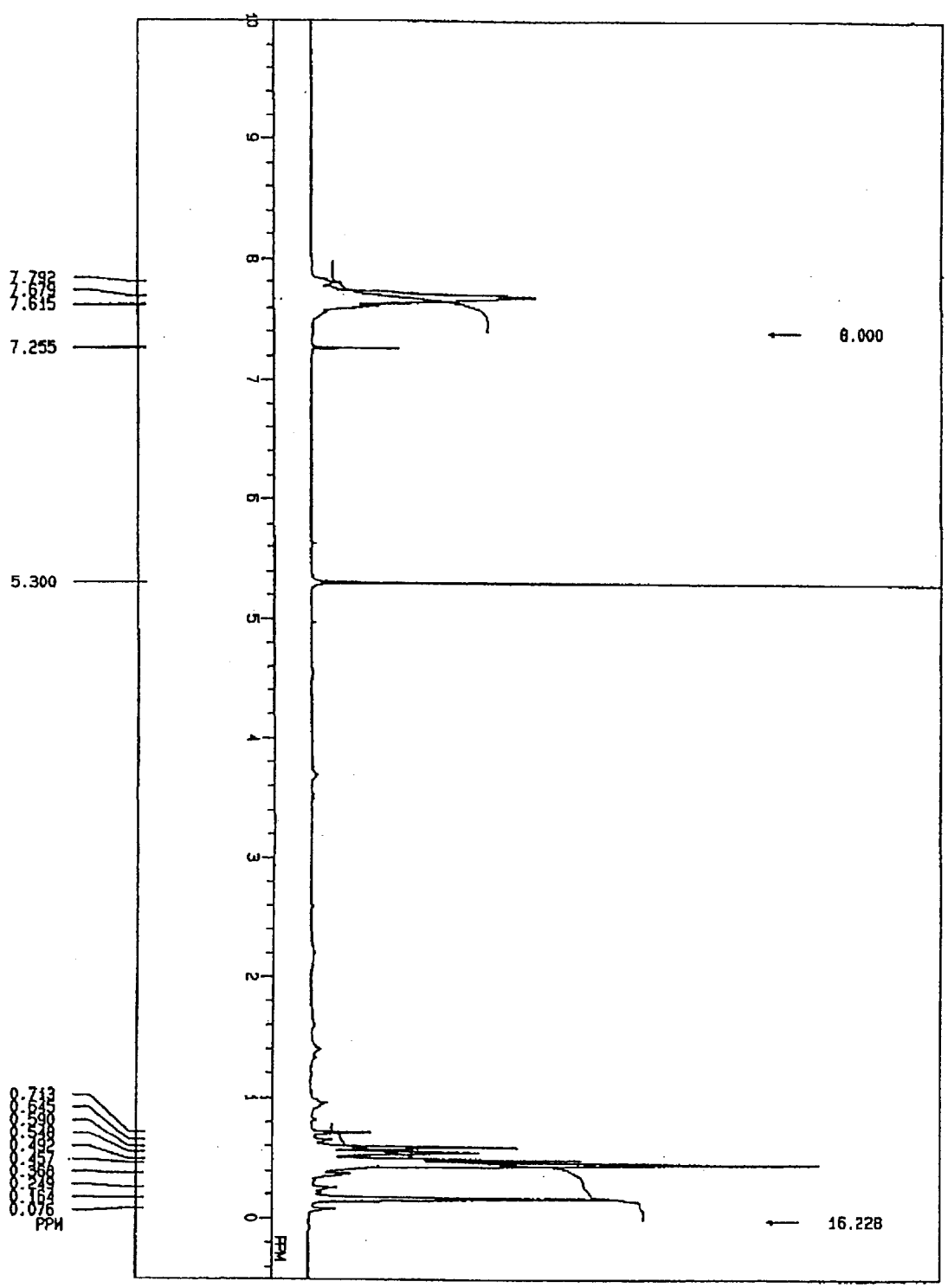
FIG. 8 shows $^1$H-NMR analytical chart of polycarbosilane of the invention obtained by the polymerization in Example 9.
Figure 9:
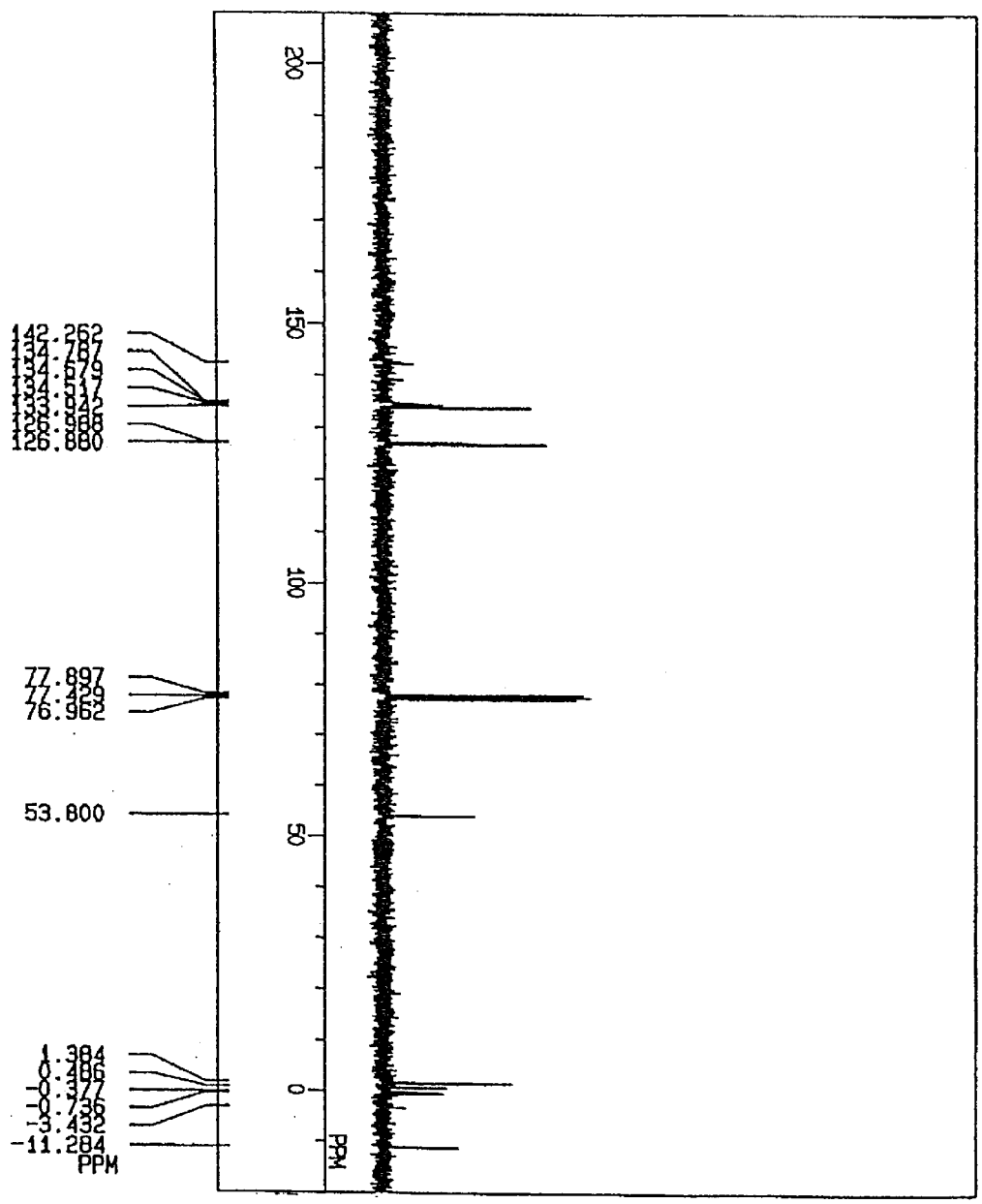
FIG. 9 shows $^{13}$C-NMR analytical chart of polycarbosilane of the invention obtained by the polymerization in Example 9.

¹H-NMR analytical chart of the polymer obtained is shown in FIG. 8, ¹³C-NMR analytical chart is shown in FIG. 9 and UV analytical chart is shown in FIG. 10.

show that the number average molecular weight (Mn) was 850 and the weight average molecular weight (Mw) was 1000.

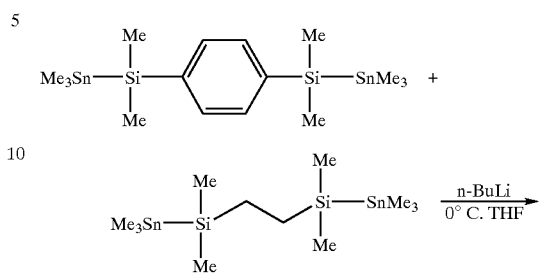

TABLE 4

| Example | —Ar— | Material (mmol) | n-BuLi (mmol) | Polymerization degree[a] | Mn[a] | Yield (%) |
|---|---|---|---|---|---|---|
| 5 | 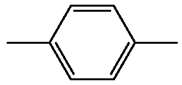 | 2.0 | 1.6 | 4.8 | $1.3 \times 10^3$ | 41<br>13[b] |
| 6 | 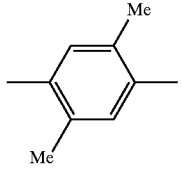 | 0.5 | 0.5 | — | — | Insoluble polymer |
| 7 |  | 0.5<br>0.5 | 0.65<br>0.77 | 4.9<br>5.5 | $1.4 \times 10^3$<br>$1.5 \times 10^3$ | >99<br>>99 |
| 8 | 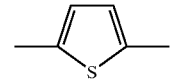 | 1.0<br>0.9 | 0.9<br>1.1 | 7.5<br>6.8 | $1.8 \times 10^3$<br>$1.7 \times 10^3$ | 23<br>31 |
| 9 | 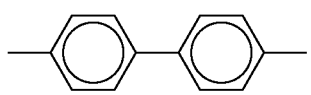 | 0.5 | 0.6 | 6.2 | $2.0 \times 10^3$ | 99 |

[a]The number average molecular weight determined by ¹H-NMR and the average polymerization degree calculated therefrom
[b]Insoluble polymers included

EXAMPLE 10

Figure 11:
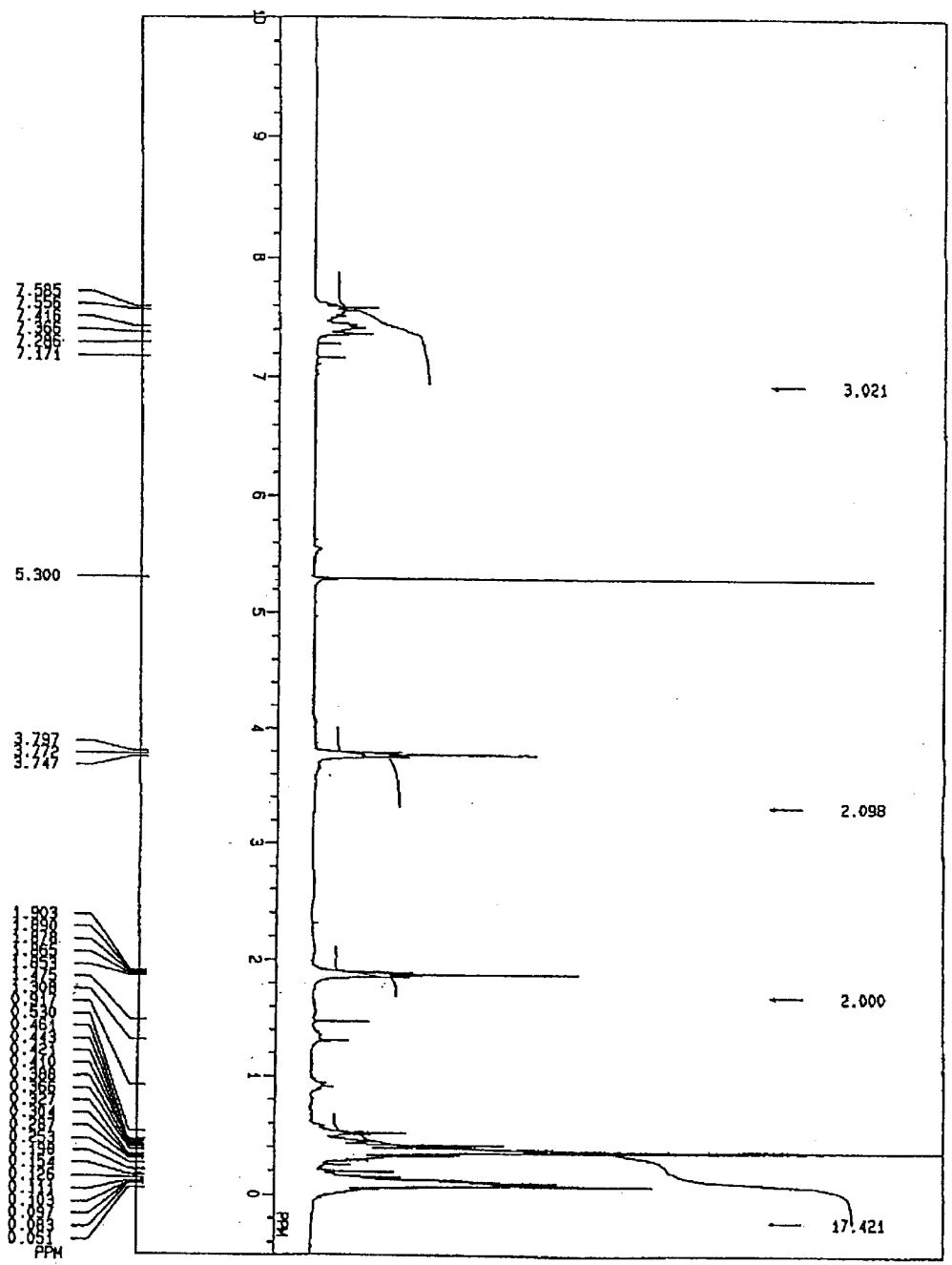
FIG. 11 shows $^1$H-NMR analytical chart of a copolymer of carbosilanes of the invention obtained by the copolymerization in Example 10.
Figure 12:
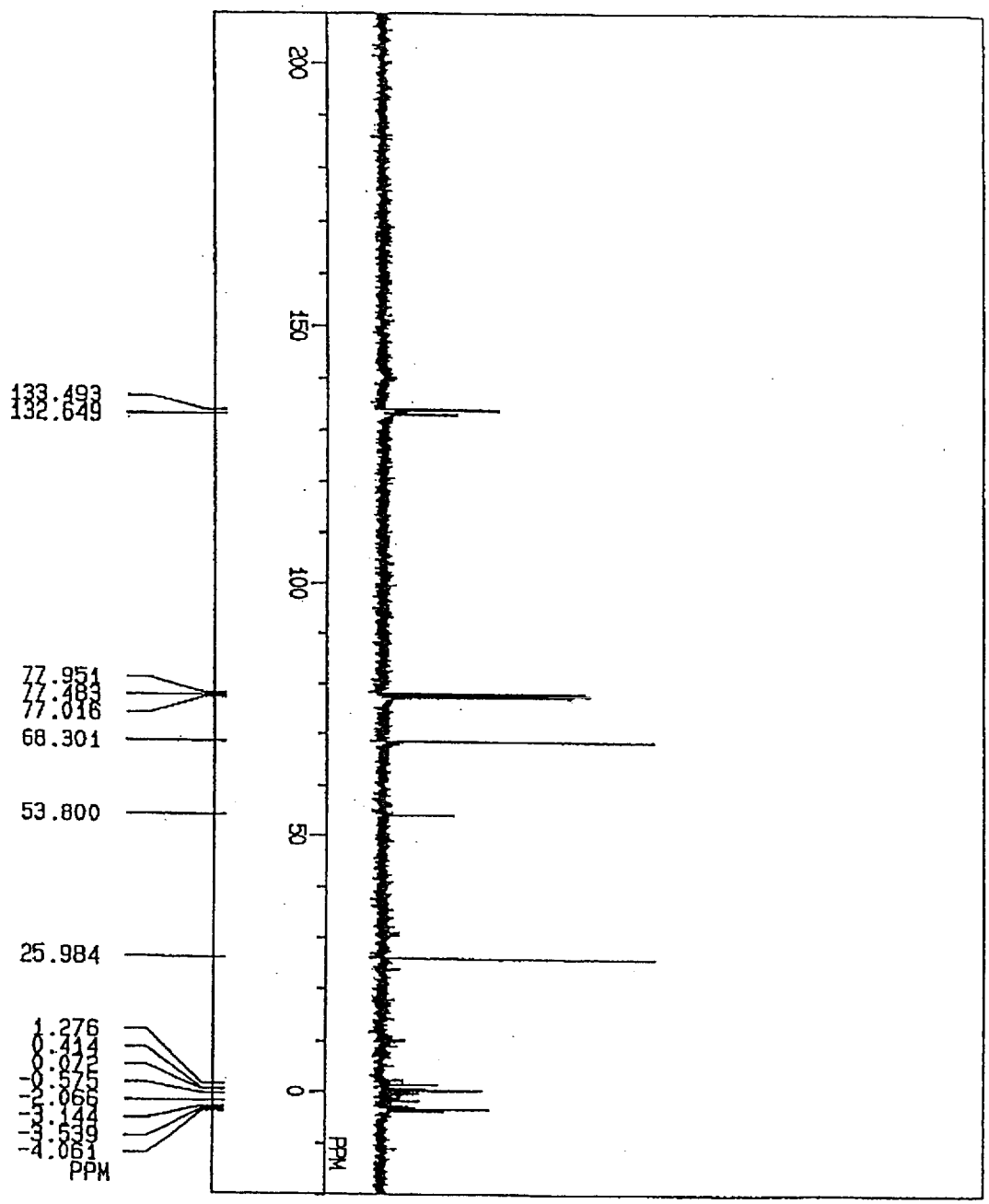
FIG. 12 shows $^{13}$C-NMR analytical chart of a copolymer of carbosilanes of the invention obtained by the copolymerization in Example 10.

Into a nitrogen-purged 30 ml three-necked flask with a septum cap and a digital thermometer were introduced 0.50 mmol of 1,4-bis(trimethylstanyldimethylsilyl)benzene (1), 0.5 mmol of 1,2-bis(trimethylstanyldimethylsilyl)ethane (2) and 4.0 ml of THF, and the mixture was maintained at 0° C. A hexane solution containing 1.0 mmol of n-BuLi was added slowly to the mixed solution. After 12 hours, the reaction terminated by addition of 5 ml of water. The reaction solution was extracted with chloroform, the extract was passed through a silica gel column, followed by fractionation using hexane and THF. ¹H-NMR analytical chart of a fraction eluted with hexane is shown in FIG. 11 and ¹³C-NMR analytical chart is shown in FIG. 12. These charts indicate that the polymer is a copolymer of the above compounds (1) and (2). Further, the results of GPC analysis -continued

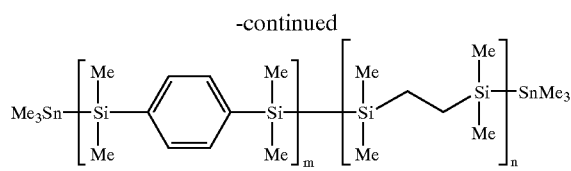

EFFECT OF THE INVENTION

A molecular weight degree controllable polycarbosilane can be synthesized by employing the present carbosilane having a specific organometallic terminal group as a material and an organic typical metal compound as an initiator. Further, the novel carbosilane and polycarbosilane of the present invention per se are useful as industrial materials, but they are also usable as materials for polymers as a macromonomer.

What is claimed is:

1. A carbosilane represented by the following general formula (1):

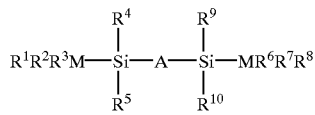

wherein M represents an Sn or Pb atom; A represents an aliphatic group having 2–10 carbon atoms, a carbocyclic group or a heterocyclic group containing one or more atoms selected from silicon, oxygen, nitrogen and sulfur atoms, both groups having 6–30 carbon atoms; $R^1$, $R^2$, $R^3$, $R^6$, $R^7$ and $R^8$ each independently represent an alkyl group having 1–20 carbon atoms, an alkenyl or alkynyl group having 2–20 carbon atoms, or an aryl group having 6–20 carbon atoms; and $R^4$, $R^5$, $R^9$ and $R^{10}$ each independently represent an alkyl group having 1–20 carbon atoms, an alkenyl or alkynyl group having 2–20 carbon atoms, an alkenylalkyl or alkynylalkyl group having 3–20 carbon atoms, or an aryl group having 6–20 carbon atoms.

2. A carbosilane according to claim 1 in which M represents an Sn atom.

3. A carbosilane according to claim 1 in which A represents 1,4-phenylene, 2,5-dimethyl-1,4-phenylene, 1,4-xylylene, 1,4-thiophene or 4,4'-biphenylene.

4. A carbosilane according to claim 1 in which each of $R^1$, $R^2$, $R^3$, $R^4$, $R^5$, $R^6$, $R^7$, $R^8$, $R^9$ and $R^{10}$ is a methyl group.

5. A polycarbosilane represented by the following general formula (2) whose weight average molecular weight in terms of polystyrene is 800–100,000:

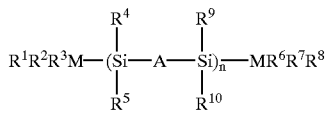

wherein M represents an Sn or Pb atom; A represents an aliphatic group having 2–10 carbon atoms, a carbocyclic group or a heterocyclic group containing one or more atoms selected from silicon, oxygen, nitrogen and sulfur atoms, both groups having 6–30 carbon atoms; $R^1$, $R^2$, $R^3$, $R^6$, $R^7$ and $R^8$ each independently represent an alkyl group having 1–20 carbon atoms, an alkenyl or alkynyl group having 2–20 carbon atoms, or an aryl group having 6–20 carbon atoms; $R^4$, $R^5$, $R^9$ and $R^{10}$ each independently represent an alkyl group having 1–20 carbon atoms, an alkenyl or alkynyl group having 2–20 carbon atoms, an alkenylalkyl or alkynylalkyl group having 3–20 carbon atoms, or an aryl group having 6–20 carbon atoms; and $1<n\leq 500$.

6. A polycarbosilane according to claim 5 in which M represents an Sn atom.

7. A polycarbosilane according to claim 5 or 6 in which A represents 1,4-phenylene, 2,5-dimethyl-1,4-phenylene, 1,4-xylylene, 1,4-thiophene or 4,4'-biphenylene.

8. A polycarbosilane represented by the following general formula (3) whose weight average molecular weight in terms of polystyrene is 800–100,000:

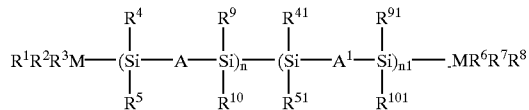

wherein, M represents an Sn, Ge, or Pb atom; A and $A^1$ each independently represent an aliphatic group having 2–10 carbon atoms, a carbocyclic group or a heterocyclic group containing one or more atoms selected from silicon, oxygen, nitrogen and sulfur atoms, both groups having 6–30 carbon atoms; $R^1$, $R^2$, $R^3$, $R^6$, $R^7$ and $R^8$ each independently represent an alkyl group having 1–20 carbon atoms, an alkenyl or alkynyl group having 2–20 carbon atoms, or an aryl group having 6–20 carbon atoms; $R^4$, $R^5$, $R^9$, $R^{10}$, $R^{41}$, $R^{51}$, $R^{91}$ and $R^{101}$ each independently represent an alkyl group having 1–20 carbon atoms, an alkenyl or alkynyl group having 2–20 carbon atoms, an alkenylalkyl or alkynylalkyl group having 3–20 carbon atoms, or an aryl group having 6–20 carbon atoms; and $1\leq n\leq 499$, $1\leq n1\leq 499$ and $2\leq n+n1\leq 500$, provided that the two structural units for carbosilane are not identical each other.

9. A polycarbosilane according to claim 8 in which M represents an Sn atom.

10. A polycarbosilane according to claim 8 or 9 in which A represents 1,4-phenylene, 2,5-dimethyl-1,4-phenylene, 1,4-xylylene, 1,4-thiophene or 4,4'-biphenylene.

11. A process for producing a polycarbosilane represented by the general formula (2)

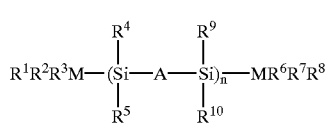

wherein M represents an Sn, Ge or Pb atom; A represents an aliphatic group having 2–10 carbon atoms, a carbocyclic group or a heterocyclic group containing one or more atoms selected from silicon, oxygen, nitrogen and sulfur atoms, both groups having 6–30 carbon atoms; $R^1$, $R^2$, $R^3$, $R^6$, $R^7$ and $R^8$ each independently represent an alkyl group having 1–20 carbon atoms, an alkenyl or alkynyl group having 2–20 carbon atoms, or an aryl group having 6–20 carbon atoms; $R^4$, $R^5$, $R^9$ and $R^{10}$ each independently represent an alkyl group having 1–20 carbon atoms, an alkenyl or alkynyl group having 2–20 carbon atoms, an alkenylalkyl or alkynylalkyl group having 3–20 carbon atoms, or an aryl group having 6–20 carbon atoms; and $1<n\leq 500$, or the general formula (3)

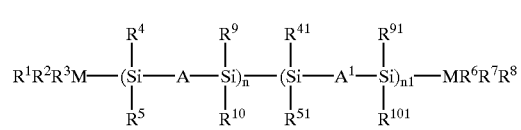

wherein M, A, $R^1$, $R^2$, $R^3$, $R^4$, $R^5$, $R^6$, $R^7$, $R^8$, $R^9$ and $R^{10}$ are as defined above; $A^1$ has the same meaning as A; $R^{41}$, $R^{51}$, $R^{91}$ and $R^{101}$ have the same meaning as $R^4$, $R^5$, $R^9$ and $R^{10}$, respectively; and $1\leq n\leq 499$, $1\leq n1\leq 499$ and $2\leq n+n1\leq 500$, provided that the two structural units for carbosilane are not identical each other, which comprises reacting the same or different kinds of carbosilanes represented by the general formula (1)

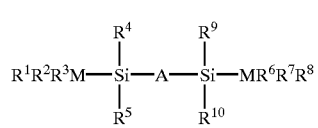

wherein M, A, $R^1$, $R^2$, $R^3$, $R^4$, $R^5$, $R^6$, $R^7$, $R^8$, $R^9$ and $R^{10}$ are as defined above, using an organic lithium, sodium, magnesium, calcium or zinc compound as an initiator.

* * * * *